United States Patent [19]
Chenevert et al.

[11] Patent Number: 5,639,427
[45] Date of Patent: Jun. 17, 1997

[54] SULFURIC ACID PREPARATION ASSEMBLY

[75] Inventors: Paul J. Chenevert; Peter Stone, both of Austin, Tex.

[73] Assignee: Ashland Inc., Columbus, Ohio

[21] Appl. No.: 378,350

[22] Filed: Jan. 26, 1995

[51] Int. Cl.⁶ .................................................. B01L 3/00
[52] U.S. Cl. .......................... 422/102; 422/99; 422/104; 159/22; 159/23; 159/DIG. 19; 159/DIG. 42; 202/244; 202/245; 220/327; 220/328; 220/367.1; 220/378
[58] Field of Search ....................... 422/99, 100, 101, 422/102, 104, 113, 242; 202/266, 163, 245, 244, 267.1; 159/22, 21, 23, DIG. 15, DIG. 19, DIG. 42; 220/327, 328, 378, 367.1

[56] References Cited

U.S. PATENT DOCUMENTS

| | | | |
|---|---|---|---|
| 3,079,033 | 2/1963 | Wootton | 220/327 X |
| 3,294,650 | 12/1966 | Manteufel | 159/DIG. 19 X |
| 3,652,229 | 3/1972 | Burke | 159/22 X |
| 4,135,640 | 1/1979 | MacQuilkin et al. | 220/316 |
| 4,138,309 | 2/1979 | Kuhnlein et al. | 159/13 A |
| 4,251,715 | 2/1981 | Petersson et al. | 219/284 |
| 4,313,786 | 2/1982 | Smith | 159/22 |
| 4,354,899 | 10/1982 | Broberg et al. | 159/13 A |
| 4,434,026 | 2/1984 | Hawis | 159/15 |
| 4,444,331 | 4/1984 | Lankston | 220/304 |
| 4,703,935 | 11/1987 | Scherping | 277/1 |
| 4,837,161 | 6/1989 | Stevens et al. | 436/52 |
| 4,889,693 | 12/1989 | Su et al. | 422/113 |
| 4,936,953 | 6/1990 | Abbott et al. | 202/164 |
| 4,944,923 | 7/1990 | Heinrichs et al. | 422/102 |
| 5,061,348 | 10/1991 | McCormick et al. | 202/154 |
| 5,071,140 | 12/1991 | Queuedo del Rio | 277/27 |
| 5,149,399 | 9/1992 | Kishi et al. | 159/22 |
| 5,219,007 | 6/1993 | Ebbing | 141/7 |
| 5,230,812 | 7/1993 | Williams | 210/767 |
| 5,230,865 | 7/1993 | Hargett et al. | 422/113 |
| 5,267,791 | 12/1993 | Christian et al. | 366/249 |
| 5,338,409 | 8/1994 | Heierli | 202/205 |

*Primary Examiner*—Harold Pyon
*Attorney, Agent, or Firm*—Louis E. Marn

[57] ABSTRACT

An assembly for prepping sulfuric acid for spectrometric analysis comprised of a vessel member having sleeve members formed with channels disposed about an outer peripheral surface and a cap member including a disc shaped top portion and a lower body portion and further including a gasket member to be positioned between the cap member and the vessel member wherein the lower body portion extending into a chamber of the vessel member and wherein the top portion includes channels to be aligned with the channels of the sleeves of the vessel member for receiving mounting devices for rigidly mounting the cap member to the vessel member.

5 Claims, 1 Drawing Sheet

SULFURIC ACID PREPARATION ASSEMBLY

BACKGROUND OF THE INVENTION

1. Field of the Invention

This invention relates to spectrometric analysis, and more particularly, to an assembly for concentrating sulfuric acid and like high boiling materials for subsequent spectrometric analysis.

2. Description of Prior Art

Analyzing concentrated chemicals using spectrometric techniques usually requires the concentration (or "prepping") of the chemical sample by evaporation to a weight of a known ratio to the weight of the original sample. Such procedure allows the sample to be analyzed since it reduces the concentration of the chemical (also known as matrix removal) as well as concentrate trace contaminants thereby permitting analysis of low levels.

Prepping of sulfuric acid is particularly troublesome since high temperatures are required with concomitant evolution of toxic fumes. Originally, prepping was performed in open vessels in a clean room hood. Subsequently, prepping involved the use of a covered vessel or assemblies. These are disclosed vessel types used in chemical analysis, such as in U.S. Pat. No. 3,324,628 to Nelson; U.S. Pat. No. 4,703,935 to Scherping, U.S. Pat. No. 4,837,161 to Stevens et al. and U.S. Pat. No. 4,401,625 to Willay et al.

The handling of the toxic fumes constantly presented a problem, such as, for example, by leakage through gaskets and the like. Use of inert gas flow and the like proved unsuccessful as well as the inability of vessel assemblies to maintain gaseous integrity at the high temperature levels required for sulfuric acid prepping.

OBJECTS OF THE PRESENT INVENTION

An object of the present invention is to provide an improved prepping assembly for facilely concentrating sulfuric acid for spectrometric analysis.

Another object of the present invention is to provide an improved prepping assembly permitting safe handling of toxic fumes during prepping of sulfuric acid for spectrometric analysis.

Still another object of the present invention is to provide an improved prepping assembly which may be readily assembled or disassembled during usage.

Yet another object of the present invention is to provide an improved prepping assembly of improved vapor integrity.

SUMMARY OF THE INVENTION

There is described an assembly for prepping sulfuric acid for spectrometric analysis comprised of a vessel member having sleeve members formed with channels disposed about an outer peripheral surface and a cap member including a disc shaped top portion and a lower body portion and further including a gasket member to be positioned between the cap member and the vessel member wherein the lower body portion extending into a chamber of the vessel member and wherein the top portion includes channels to be aligned with the channels of the sleeves of the vessel member for receiving mounting devices for rigidly mounting the cap member to the vessel member.

BRIEF DESCRIPTION OF THE DRAWINGS

Further objects and advantages of the present invention will become more readily apparent from the following detailed description when taken with the accompanying drawings wherein.

DETAILED DESCRIPTION OF THE INVENTION

Figure 1:
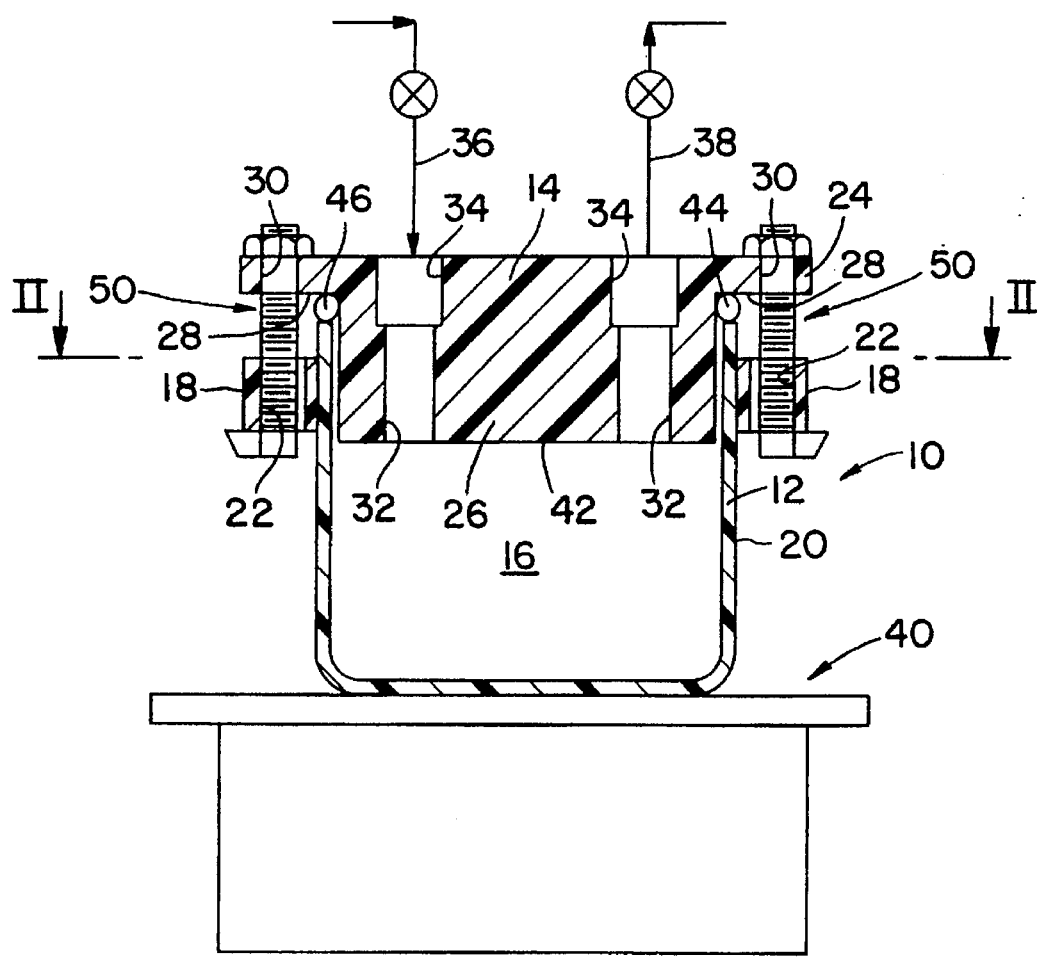
FIG. 1 is a cross-sectional view, somewhat schematic, of the spectrometric sample preparation assembly of the present invention.
Figure 2:
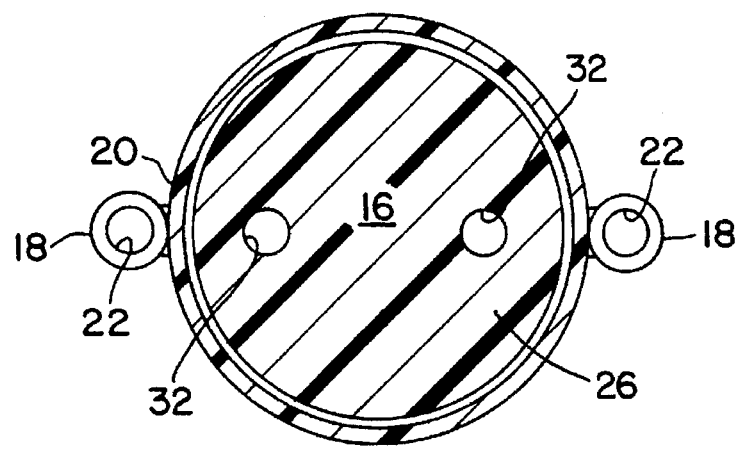
FIG. 2 is a cross-sectional view of the spectrometric sample preparation assembly of the present invention taken along the lines II—II of FIG. 1.

Referring now to the drawings, there is illustrated a spectrometric sample preparation assembly of the present invention, generally indicated as 10, comprised of a cylindrically-shaped vessel member 12 enclosed by a cap or cover member 14. The vessel member 12 defines a chamber 16 and is provided with a plurality of sleeve members 18 (two shown) radially disposed about an outer surface portion 20 of the vessel member 12. Each sleeve member 18 is formed with cylindrically-shaped channel 22 having an axis parallel to the major axis of the vessel member 12. The vessel member 12 is formed of a material of high heat tolerance at temperatures greater than about 300° C., such as quartz, sold under the name "224LD" by General Electric Company.

The cap or cover member 14 is generally T-shaped in cross-section formed of an upper circularly-shaped disc portion 24 and a lower cylindrically-shaped body portion 26. The upper disc portion 24 is of a diameter substantially greater than the diameter of the vessel member 12 and the lower body portion 26 thereby defining a lower supporting surface 28. The upper disc portion 24 of the cap member 14 is provided with cylindrically-shaped channels 30 to be aligned with the channels 22 of the sleeve members 18 of the vessel member 12, as more fully hereinafter described.

The lower body portion 26 of the cap member 14 is of a diameter less than the inner diameter of the vessel member 14 thereby permitting insertion of the lower body portion 26 of the cap member 14 into the chamber 16 of the vessel member 12 during assembly after inclusion of a sample prior to prepping. The cap member 14 is formed with at least two channels 32, extending through the lower body portion 26. An upper portion 34 of each channel 30 is formed with a NPT thread permitting facile attachment of purge and exhaust fittings, generally indicated as 36 and 38.

The cap member 14 is formed of an acid resistant material, such as polytetrafluoroethylene. Since the vessel member 14 is placed in direct contact with a heat source, such as a hot plate, generally indicated as 40, the vessel member 12 is of high heat tolerance, whereas the cap member 14, not in direct heat transfer contact with the heat source, does not require like material specification. The body portion 26 of the cap member 14 is solid to provide weight and strength and is of a height sufficient to permit condensation to collect about a lower surface portion 42 and to fall back into the vessel member 12 thereby providing stability during handling and reflux. Generally, the lower body portion 26 of the cap member 14 extends into the chamber 16 a distance of at least about ⅓ the height of the chamber 16. The disc portion 24 of the cap member 14 is of a thickness sufficient to withstand the mounting forces. The weight of the cap member is sufficient to maintain the integrity of the chamber during refluxing in the absence of mounting or clamping forces.

A circularly-shaped O-ring member 44 is disposed between a top surface portion 46 of the vessel member 12 and supporting outer surface 46 of the lower body portion and supporting surface 28 of the upper disc portion 12 of the cap member 14. The ring member 42 is formed of an elastomeric matter having acid resistant properties, such as teflon encapsulate polyethylene and the like.

In operation, a sample to be concentrated, such as 96% (wt./wt.) sulfuric acid is introduced into the chamber 16 of the vessel member 12 and the cap member 14 together with the prepositioned O-ring member 42 is placed on the vessel member 14, such that the lower body portion 26 extends into the upper portion of the chamber 16 of the vessel member 12. The cap member 14 is positioned such that each channel 30 thereof is in alignment with the channel 22 of each sleeve member 18. Nut and bolt assemblies, generally indicated as 50, are positioned therein and finger tightened.

The vessel assembly 10 is positioned on the hot plate 40, and the fittings 36 and 38 connected to respective openings 32. The procedure includes heating to temperatures from 200° to 300° C. for from 4-6 hours while introducing an ultrapure nitrogen gas stream with acid exhaust. After heating, the mounting assemblies 50 are removed and nitric acid introduced with refluxing at about 80° C. The sample is thereafter analyzed in a spectrometer equipped with an ultrasonic nebulizer, etc.

While the invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed is:

1. A sulfuric acid prepping assembly, which comprises:

a vessel member defining a chamber and having sleeve members positioned about an outer surface of said vessel member, each of said sleeve members having a channel;

a cap member including an upper portion and a lower portion, said upper portion being of a diameter greater than a diameter of said vessel member and defining a supporting surface, said lower portion being of a diameter less than a diameter of said chamber thereby extending downwardly into said chamber a distance sufficient to permit collection of condensate, said upper portion including channels for alignment with said channels of said sleeves of said vessel member, said cap member including threaded channel means for receiving purge and exhaust conduit members;

a ring member positioned between said supporting surface of said cap member and said vessel member; and bolt assembly means for mounting said cap member to said vessel member via said channels.

2. The sulfuric acid prepping assembly as defined in claim 1 wherein said lower body portion of said cap member extends downwardly a distance of at least about ⅓ of a height of said chamber.

3. The sulfuric acid prepping assembly as defined in claim 1 wherein said vessel member is formed of a heat resistant material capable of withstanding temperatures in excess of about 300° C.

4. The sulfuric acid prepping assembly as defined in claim 1 wherein major axis of said channels of said sleeve members are parallel to a major axis of said vessel member.

5. The sulfuric acid prepping assembly as defined in claim 4 wherein said cap member is formed with cylindrically-shaped channels at a radius from said major axis substantially equal to radius of said channel of said sleeve member of said vessel member for cooperating with said mounting means.

* * * * *